United States Patent [19]

Lannert

[11] 4,228,300
[45] Oct. 14, 1980

[54] POLYCARBOXYLATE ETHERS

[75] Inventor: Kent P. Lannert, Freeburg, Ill.

[73] Assignee: Monsanto Company, St. Louis, Mo.

[21] Appl. No.: 253,357

[22] Filed: May 15, 1972

Related U.S. Application Data

[63] Continuation-in-part of Ser. No. 158,577, Jun. 30, 1971, abandoned, and a continuation-in-part of Ser. No. 158,540, Jun. 30, 1971, abandoned.

[51] Int. Cl.² ............................................. C07C 59/22
[52] U.S. Cl. .................................... 560/180; 562/583
[58] Field of Search ................... 260/535 P; 560/180; 562/583

[56] References Cited

PUBLICATIONS

E. von Rudloff et al., Canadian Journal of Chemistry, vol. 35, pp. 315–321, 1957.

*Primary Examiner*—Paul J. Killos
*Attorney, Agent, or Firm*—N. E. Willis; J. E. Maurer; F. D. Shearin

[57] ABSTRACT

Compounds having the formula

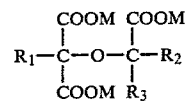

wherein M is an alkali metal or ammonium, $R_1$ and $R_2$ are hydrogen, methyl or ethyl and $R_3$ is hydrogen, methyl, ethyl or COOM are useful sequestrants and detergency builders. Lower alkyl esters and acids of such compounds are useful intermediates for their production.

10 Claims, No Drawings

POLYCARBOXYLATE ETHERS

BACKGROUND OF THE INVENTION

This application is a continuation-in-part of U.S. applications, Ser. Nos. 158,577 and 158,540, filed June 30, 1971 and June 30, 1971, both abandoned.

This invention relates to novel compounds and precursors thereof useful as sequestrants and detergency builders and to detergent formulations containing such compounds. Numerous materials are known which, by virtue of sequestering characteristics and/or capability to enhance the cleansing ability of detergent formulations in combination with various surfactants are useful in water treating applications, or as adjuvants, reenforcers, supplements, augmentors, potentiators and/or benefactors in detergent formulations wherein such materials are usually referred to as detergency builders. It is noted that although many detergency builders are also sequestrants, the determination of materials which are effective detergency builders is a complex matter emperical in nature and not accurately predictable from known characteristics of the materials.

Many materials of the foregoing type are characterized by high phosphorous content such as the alkali metal tripolyphosphates widely employed as detergency builders. It has recently been suggested by some researchers that such compounds may contribute to the acceleration of eutrophication processes. Accordingly, particularly in the detergent builder field, extensive efforts have been exerted to provide alternate functional compounds free of phosphorus.

SUMMARY OF THE INVENTION

It is an object of this invention to provide novel compounds and intermediates useful for the production of such compounds which are useful as sequestrants and as detergency builders.

The novel compounds of this invention and their manufacture and utility will be understood from the following description of the preferred embodiments.

DESCRIPTION OF THE PREFERRED EMBODIMENTS

The novel compounds of this invention are represented by the formula $$R_1-\underset{\underset{COOR}{|}}{\overset{\overset{COOR}{|}}{C}}-O-\underset{\underset{R_3}{|}}{\overset{\overset{COOR}{|}}{C}}-R_2$$

wherein R is hydrogen, methyl, ethyl, alkali metal or ammonium and $R_1$ and $R_2$ are hydrogen, methyl, or ethyl and $R_3$ is hydrogen, methyl, ethyl or COOR.

The compounds (except those in which $R_1$ and $R_2$ are hydrogen and $R_3$ is COOR) can be prepared by reacting the appropriate halomalonate,

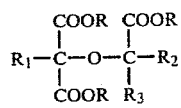

(X being —Cl when $R_1$ is hydrogen and being —Cl or —Br when $R_1$ is methyl) with the sodium salt of the appropriate α-hydroxy ester

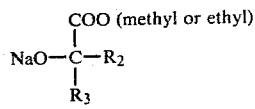

in an inert solvent such as 1,2-dimethoxyethane or tetrahydrofuran.

This reaction yields the ester forms of the compounds of this invention which are saponified by conventional techniques to yield the desired ammonium or alkali metal salts. The acid forms of the compounds of this invention are obtained by acidifying the salts. The acids can be crystallized by conventional techniques to provide useful precursors for high purity salts. It is noted that when $R_1$ is hydrogen, the acid is relatively unstable due to a tendency to undergo rapid decarboxylation.

Those compounds in which $R_3$ is COOR, including those in which $R_1$ and $R_2$ are hydrogen can be prepared by adding a solution (preferably about 1 molar) of compounds represented by the formula

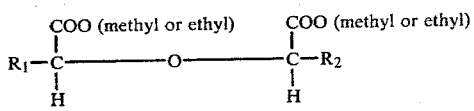

in tetrahydrofuran to two equivalents of lithium diisopropylamide in tetrahydrofuran solution (preferably about 1 molar) at a temperature of about −78° C.

It is believed that this procedure results in formation of a lithium salt represented by the formula

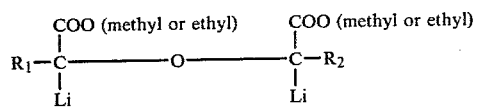

Gaseous $CO_2$ is then introduced to form

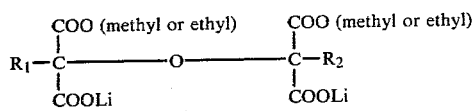

The dilithium salt is converted to a half-ester half-acid

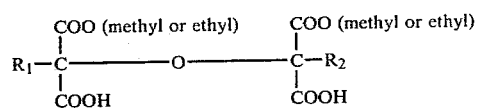

by treatment with an organic strong acid cation exchange resin, for example, a sulfonated polystyrene resin such as marketed by Fischer Scietific Co., under the trademark Rexyn ® 101(H). The ester forms can be obtained by conventional esterification procedures. The salt forms are obtained by saponification of the half-ester half-acid.

In one preferred embodiment of the invention, R is sodium and $R_1$, $R_2$ and $R_3$ are hydrogen. In another preferred embodiment, R is sodium, $R_1$ is methyl and $R_2$ and $R_3$ are hydrogen. In another preferred embodiment, R is sodium, $R_1$ and $R_2$ are hydrogen and $R_3$ is COONa. These embodiments are preferred by virtue of availability of raw materials for their manufacture and their excellent performance as detergency builders.

Both the acid and salt forms of the compounds of this invention are useful as metal ion sequestrants and as detergency builders, the use of the salt form being preferred.

The detergent formulations utilizing the compounds of this invention will contain from 1 to 75% by weight, preferably from 5 to 50% by weight of the salt, preferably sodium salt forms of the compounds of this invention. Such compounds can be utilized as the sole detergency builder in the compositions or in combination with other known detergency builders such as water soluble inorganic builder salts, for example, alkali metal carbonates, borates, phosphates, polyphosphates, bicarbonates and silicates or organic builders such as salts of phytic acid, sodium citrate, water soluble polymeric polycarboxylates as described in U.S. Pat. No. 3,308,067 and the like.

The detergent formulations will additionally contain at least 8% by weight of a surfactant. Any of the numerous well known anionic, nonionic, zwitterionic or ampholytic surfactants can be employed.

Examples of suitable anionic surfactants include alkyl ethyl sulfonates, alkyl sulfates, acyl sarcosinates; acyl esters of isocyanates, acyl N-methyl taurides, and alkyl aryl sulfonates. The foregoing materials are used in the form of their water-soluble sodium, potassium, ammonium and alkyl ammonium salts. Specific examples include sodium laryl sulfate; sodium N-methyl aluryll tauride; sodium dodecyl benzene sulfonate; and triethanol amine undecanol benzene sulfonate.

Examples of suitable nonionic detergents include alkyl phenol and alcohol alkoxylates including condensates of 1-decanol or 1-undecanol with from 3 to 5 molecular proportions of ethylene oxide such as described in U.S. patent application Ser. No. 707,480 filed Feb. 23, 1968 and copending herewith; condensates of monohydroxy or polyhydroxy alcohols such as oleyl alcohol or 1-tridecanol with from 9 to 15 molecular proportions of ethylene oxides; alkyl internal vicinal dialkoxy or hydroxy alkoxy compounds as described in U.S. patent application Ser. No. 852,898 filed Aug. 25, 1969 and copending herewith; and condensates of alkylene oxides with organo amines, for example, ethylene diamine and amides such as N-octadecyl diethanol amide.

Suitable ampholitic surfactants include the amido alkene sulfonates such as sodium C-pentadecyl, N-methyl amido ethyl sulfonate potassium C-octyl N-napthalene amido propyl sulfonate; ammonium C-decyl, N-cyclo propyl amido butyl sulfonate, and aliphatic amine derivatives in which the aliphatic substituent contains an anionic water-solubilizing substituent such as a carboxy, sulfo, phosphato, or phosphino group, for example, sodium-3-dodecyl amino propionate and sodium-3-dodecyl amino propane sulfonate.

Examples of zwitterionic surfactants include derivatives of quaternary ammonium phosphonium and sulfonium compounds such as 3-(N,N-dimethyl-N-hexadecyl ammonio) propane-1-sulfonate and 3-(N,N-dimethyl-N-hexadecyl ammonio-2-hydroxy propane-1-sulfonate).

It will be understood that the above examples of supplementary surfactants are by no means comprehensive. Numerous other surfactants are known to those skilled in the art and are set forth in such familiar references as Surface Active Agents by A. M. Schwarz and James W. Perry. It will be further understood that the use of such surfactants will be in accordance with conventional, well-understood practices of detergent formulation. For example, cationic and anionic detergents will not normally be employed in combination due to recognized problems of precipitation of insoluble products.

In accordance with general practice, the ratio of the detergency building components to the surfactant components will be in the range of from 1:2 to about 12:1 by weight.

In addition to surfactant and builder components, the detergent formulations may contain fillers such as sodium sulfate and minor amounts of bleaches, dyes, optical brighteners, soil anti-redeposition agents, perfumes and similar conventional detergent formulation additives.

It is further expected that the compounds of this invention will function effectively in machine dishwashing formulations as total or partial replacements for sodium tripolyphosphate.

The invention is further illustrated by the following Examples wherein all parts and percentages are by weight unless otherwise indicated.

EXAMPLE I

To a slurry of 34 grams sodium ethyl glycolate in 300 ml of 1,2-dimethoxyethane is added with stirring to a solution of 63 grams diethyl 2-bromo-2-methylmalonate in 100 ml of 1,2-dimethyoxyethane precooled to 5° C. During slurry addition, the temperature is maintained below 10° C. The reaction mixture is maintained at 25° C. for 16 hours and at 65° C. for 2 hours with stirring. Solids are recovered by filtration and solvent removed under reduced pressure. The residue is dissolved in $CHCl_3$ and the solution is washed, in succession, with 0.5 normal HCl, saturated $Na_2CO_3$, and water. The solution is then dried over anhydrous $MgSO_4$ and the $CHCl_3$ removed under reduced pressure. The residue is fractionally distilled with product being collected at 95°–97° C., 0.04 mm Hg.

The product is identified as triethyl 2-oxa-1,3,3-butane tricarboxylate by nuclear magnetic resonance and elemental analysis.

The ester is saponified in an aqueous ethanol solution of sodium hydroxide at room temperature. Acidifying the solution with $H_2SO_4$ yields the acid which is extracted with ether and crystallized therefrom.

Pouring the saponified solution into excess methanol precipitates the salt.

EXAMPLE II

The salt and acid produced according to Example I are tested for sequestration characteristics and are found to effectively sequester $Ca^{++}$ ions.

EXAMPLE III

Detergent formulations containing 12% linear alkylbenzene sulfonate having an average alkyl chain length of about 12 carbon atoms from 5 to 75% trisodium 2-oxa-1,3,3-butanetricarboxylate; 12% sodium silicate having an $SiO_2$ to $Na_2O$ ratio of about 2.4; and a quantity of sodium sulfate sufficient to equal 100% are found, in conventional laundry operations, to clean soiled samples of cotton and polyester cotton broadcloth substantially better than otherwise identical formulations containing no trisodium 2-oxa-1,3,3-butanetricarboxylate. These tests demonstrate that this material is an effective detergency builder material.

EXAMPLE IV

The tests of Example III above are repeated using a detergent formulation in which Neodol 45-11 (a nonionic surfactant which is an aduct of a modified oxo type $C_{14}$–$C_{15}$ alcohol with an average of 11 moles of ethylene oxide is substituted for the alkylbenzene sulfonate. Comparable results are obtained.

EXAMPLE V

The tests of Example III are repeated with a detergent formulation wherein sodium hydroxyalkyl ($C_{14}$–$C_{16}$ alkyl chain length) N-methyl laurate, and ampholytic surfactant, is substituted for the alkylbenzene sulfonate. Comparable results are obtained.

EXAMPLE VI

The tests of Example III are repeated with a detergent formulation wherein cocodimethylsulfopropylbetaine, a zwitterionic surfactant is substituted for the alkylbenzene sulfonate. Comparable results are obtained.

EXAMPLE VII

To a slurry of 72 grams of sodium ethyl glycolate in 350 ml of 1,2-dimethoxyethane at 50°–65° C. is added 97 grams of diethyl chloromalonate over a two hour period. The resulting solution is refluxed until a neutral pH is obtained. The reaction mix is then stirred for 16 hours at 25° C. and reaction product isolated as in Example I, the product being collected at 119°–120° C., 0.05 mm Hg. The product is identified as triethyl 2-oxa-1,1,3-propanetricarboxylate. Salts and acid forms of the product are prepared as in Example I and are found to be effective sequestrant for $Ca^{++}$ ions.

EXAMPLE VIII

Detergent formulations containing from 5%–75% trisodium 2-oxa-1,1,2-propanetricarboxylate are prepared and tested as in Examples III–VI. Comparable results are obtained.

EXAMPLE IX

A solution of 63 gms diethyl 2-bromo-2-ethylmalonate in 25 ml tetrahydrofuran is added to a slurry of 59 gms sodium diethylmethyltartronate in 300 ml tetrahydrofuran at 65° C. The mixture is refluxed for 18 hours after which the tetrahydrofuran is removed under vacuum and the residue diluted with ethyl ether. The ethereal solution is washed with water to remove NaBr, dried over anhydrous $CaSO_4$ and distilled to remove the ether.

The residue is fractionally distilled, product being collected at 130°–135° C. (0.06 mm Hg). The product is identified as tetraethyl 3-oxa-2,2,4,4-hexanetetracarboxylate by nuclear magnetic resonance and elemental analysis.

The sodium salt is obtained by saponification in a methanol solution of sodium hydroxide at room temperature and recovered by filtration.

EXAMPLE X

To a slurry of 34 grams sodium ethyl glycolate in 300 ml tetrahydrofuran cooled to about 3° C. is added a solution of 63 grams diethyl 2-bromo-2-ethylmalonate in 25 ml tetrahydrofuran at about 3° C. The mixture is maintained at 0°–5° C. with stirring for 2 hours, warmed to and maintained at about 25° C. for 16 hours and then refluxed for 2 hours.

The tetrahydrofuran is removed under vacuum and the residue treated as in Example IX, the ester product triethyl-2-oxa-1,3,3-pentanetricarboxylate being collected at 101° C.–107° C. (0.05 mm Hg) and converted to the salt form as described in Example IX.

EXAMPLE XI

Sodium ethyl lactate (38 grams) and diethyl 2-bromo-2-ethylmalonate are reacted according to the procedure of Example X to yield an ester product triethyl-3-oxa-2,4,4-hexanetricarboxylate being collected at 92° C.–96° C. (0.04 mm Hg) which is converted to the salt form as described in Example X.

EXAMPLE XII

To a slurry of 98 grams of sodium ethyl lactate in 400 ml 1,3-dimethoxyethane at R.T. is added 136 grams diethyl chloromalonate. The mixture is heated at 70° C. for 8 hours and then maintained at 25° C. for 48 hours. The 1,2-dimethoxyethane is evaporated and the residue dissolved in carbon tetrachloride, washed with water to remove NaCl, dried over $MgSO_4$ and the $CHCl_3$ evaporated. Fractional distillation of the residue gives a product (b.p. 94° C.–96° C. at 0.03 mm Hg) analytically identified as triethyl 2-oxa-1,1,3-butanetricarboxylate. Saponification of the ester with NaOH yields trisodium 2-oxa-1,1,3-butanetricarboxylate.

EXAMPLE XIII

To a slurry of 77 grams of sodium ethyl lactate in 300 ml 1,2-dimethoxyethane at 45° C. is added a solution of 127 gms diethyl 2-bromo-2-methylmalonate in 1,2 dimethoxyethane and the temperature is allowed to rise to about 65° C. The mixture is refluxed until the pH of a water solution of the mixture is about 7. The 1,2-dimethoxyethane is evaporated, the residue washed with water to remove NaBr. Distillation of the dried residue yields a product (coolected at 82° C., 0.05 mm Hg) analytically identified as triethyl 3-oxa-2,2,4-pentanetricarboxylate. Saponification of the ester with NaOH yields trisodium 3-oxa-2,2,4-pentanetricarboxylate.

EXAMPLE XIV

A 1 liter flask is purged with nitrogen, charged with 400 ml tetrahydrofuran and cooled to −30° C. in a dry-ice acetone bath. 115 ml 2.3 molar solution of n-butyllithium in tetrahydrofuran is added and the solution cooled to −75° C. A solution of 21 gms diethyl clycolate in 100 ml tetrahydrofuran is added, the temperature being maintained below 70° C. $CO_2$ is then bubbled into the mixture for about an hour and the mixture warmed to room temperature, the tetrahydrofuran is evaporated leaving a yellow powder. The powder is dissolved in water and 100 ml of Rexyn ® 101(H) ion exchange resin added. An insoluble gum separates and is removed. The remaining solution is then passed through a column packed with sufficient resin to complete the conversion to the half-ester half-acid.

The water solution of half-acid half-ester product is dried to a syrup. This material is dissolved in 25 ml ethanol, 40 ml benzene and 0.2 gms concentrated $H_2SO_4$. Water is azeotropically removed and the residue diluted with benzene, washed with $NaHCO_3$ solution and then water and dried over $MgSO_4$. The benzene is evaporated and the residue distilled. Product collected at 141° C.–142° C. (0.05–0.1 mm Hg) is identified as tetraethyl 2-oxa-1,1,3,3-propanetetracarboxylate.

Alternatively, saponification of the half-acid half-ester with sodium hydroxide yields tetrasodium 2-oxa-1,1,3,3-propanetetracarboxylate.

EXAMPLE XV

To a slurry of 56 grams sodium diethyl methyltartronate in 300 ml of refluxing tetrahydrofuran is added a solution of 63 grams diethyl-2-bromo-2-methylmalonate in 25 ml tetrahydrofuran and the mixture is refluxed for about 16 hours. The solvent is evaporated and the residue diluted with ethyl ether. NaBr is removed by washing the ethereal solution with water and the washed solution is dried over $CaSO_4$ and $MgSO_4$ and solvent evaporated.

Distillation of the residue yields a fraction collected at 125° C. (0.05 mm Hg) identifiable as tetraethyl-3-oxa-2,2,4,4-pentanetetracarboxylate.

Saponification with NaOH yields the tetrasodium salt.

EXAMPLE XVI

Detergent formulations containing 5%–75% of the salt forms of the compounds produced according to Examples IX–XV are prepared and tested as in Examples III–VI. Comparable results are obtained.

What is claimed is:

1. Compounds having the formula

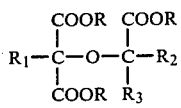

wherein R is selected from the group consisting of hydrogen, methyl, ethyl, alkali metal and ammonium; $R_1$ and $R_2$ are selected from the group consisting of hydrogen, methyl, and ethyl; and $R_3$ is selected from the group consisting of hydrogen, methyl, ethyl and COOR.

2. The compounds of claim 1 wherein R is sodium.

3. A compound according to claim 1 wherein $R_1$, $R_2$, and $R_3$ are hydrogen.

4. A compound according to claim 1 wherein $R_1$ is methyl and $R_2$ and $R_3$ are hydrogen.

5. A compound according to claim 1 wherein $R_1$ and $R_2$ are methyl and $R_3$ is hydrogen.

6. A compound according to claim 1 wherein $R_2$ is methyl and $R_1$ and $R_3$ are hydrogen.

7. A compound according to claim 1 wherein $R_3$ is COOR.

8. A compound according to claim 7 wherein $R_1$ and $R_2$ are hydrogen.

9. A compound according to claim 7 wherein $R_1$ and $R_2$ are methyl.

10. A compound according to claim 7 wherein $R_1$ is methyl and $R_2$ is hydrogen.

* * * * *